(12) United States Patent
Lee

(10) Patent No.: US 7,905,865 B2
(45) Date of Patent: Mar. 15, 2011

(54) MEDICINAL LIQUID SUPPLY APPARATUS HAVING FIXED-TYPE MEDICINAL LIQUID SUPPLY VOLUME CONTROLLER AND ARBITRARY MEDICINAL LIQUID SUPPLY VOLUME CONTROLLER

(75) Inventor: Jong-Woo Lee, Seoul (KR)

(73) Assignee: Ace Medical Co., Ltd., Goyang-Si (KR)

( * ) Notice: Subject to any disclaimer, the term of this patent is extended or adjusted under 35 U.S.C. 154(b) by 90 days.

(21) Appl. No.: 12/326,703

(22) Filed: Dec. 2, 2008

(65) Prior Publication Data

US 2010/0057015 A1  Mar. 4, 2010

(30) Foreign Application Priority Data

Sep. 3, 2008  (KR) .................. 10-2008-0086866
Sep. 26, 2008 (KR) .................. 10-2008-0094676

(51) Int. Cl.
*A61M 5/178*  (2006.01)
*A61M 37/00*  (2006.01)
*A61M 1/00*  (2006.01)

(52) U.S. Cl. ......... 604/185; 604/132; 604/153; 604/212

(58) Field of Classification Search .............. 604/32, 604/167.05, 284, 93.01, 131, 132, 151, 153, 604/185, 212, 264, 890.1
See application file for complete search history.

(56) References Cited

U.S. PATENT DOCUMENTS 3,411,534 A * 11/1968 Rose ............................ 137/595
4,191,184 A *  3/1980 Carlisle ....................... 604/153
6,500,156 B1* 12/2002 Stansbury ................... 604/185

* cited by examiner

*Primary Examiner* — Kevin C Sirmons
*Assistant Examiner* — Bradley J Osinski
(74) *Attorney, Agent, or Firm* — Jefferson IP Law, LLP

(57) ABSTRACT

Disclosed therein is a medicinal liquid supply apparatus, which includes a fixed-type medicinal liquid supply volume controller adapted to supply medicinal liquid only as much as a paramedic sets and fixes and an arbitrary medicinal liquid supply volume controller adapted to allow a patient or the third party to arbitrarily supply the medicinal liquid as occasion demands during the paramedic's absence, thereby effectively supplying the medicinal liquid according to the patient's disease and pain conditions. The medicinal liquid supply apparatus includes: a fixed-type medicinal liquid supply volume controller having a plurality of medicinal liquid branch hoses opened and closed by a controller and a medicinal liquid transfer hose always opened, the medicinal liquid branch hoses and the medicinal liquid transfer hose being connected to an inflow part and an outflow part of a medicinal liquid control line thereof; and an arbitrary medicinal liquid supply volume controller connected to a double medicinal liquid hose having a branch tube connected to the medicinal liquid transfer hose of the fixed-type medicinal liquid supply volume controller, the arbitrary medicinal liquid supply volume controller having a medicinal liquid storing tube for storing the medicinal liquid transferred through the double medicinal liquid hose to arbitrarily and additionally supply the medicinal liquid by a button body.

11 Claims, 11 Drawing Sheets

MEDICINAL LIQUID SUPPLY APPARATUS HAVING FIXED-TYPE MEDICINAL LIQUID SUPPLY VOLUME CONTROLLER AND ARBITRARY MEDICINAL LIQUID SUPPLY VOLUME CONTROLLER

This application claims benefit of priority to Republic of Korea Application No. 10-2008-0094676 filed Sep. 26, 2008 and Republic of Korea Application No. 10-2008-0086866 filed Sep. 3, 2008, the contents of which are incorporated in their entirety herein by reference.

BACKGROUND OF THE INVENTION

1. Field of the Invention

The present invention relates to a medicinal liquid supply apparatus, and more particularly, to a medicinal liquid supply apparatus, which includes a fixed-type medicinal liquid supply volume controller adapted to supply medicinal liquid only as much as a paramedic sets and fixes and an arbitrary medicinal liquid supply volume controller adapted to allow a patient or the third party to arbitrarily supply the medicinal liquid as occasion demands during the paramedic's absence, thereby effectively supplying the medicinal liquid according to the patient's disease and pain conditions.

2. Background Art

In general, as shown in FIG. 8, a conventionally used medicinal liquid supply apparatus includes: a medicinal liquid supplier 100, which is filled with medicinal liquid of a predetermined volume; a medicinal liquid hose 200 whose one end is connected to an outlet of the medicinal liquid supplier 100; a medicinal liquid volume controller 300 mounted on one portion of the medicinal liquid hose 200 for controlling a volume of the medicinal liquid discharged from the medicinal liquid supplier 100 according to a patient's disease and pain conditions; and a syringe connector 400 connected to the other end of the medicinal liquid hose 200 for inject the medicinal liquid to the patient.

However, as shown in FIG. 9, the medicinal liquid volume controller 300 provided to the medicinal liquid supply apparatus includes: a case 301; a medicinal liquid storing tube 303 formed inside the case 301 for storing some of the medicinal liquid discharged from the medicinal liquid supplier 100; and a button body 302 repeatedly actuated in such a way as to repeatedly pressurize the medicinal liquid storing tube 303 to thereby discharge the medicinal liquid of the medicinal liquid storing tube 303 by a predetermined volume. Since the medicinal liquid stored in the medicinal liquid storing tube is supplied by pressing the button body 302 once, it is impossible to control the volume of the medicinal liquid minutely.

Accordingly, the conventional medicinal liquid supply apparatus can be applied to general patients, but cannot be applied to patients, who require a minute supply of a fixed quantity or may die of shock due to an excessive supply of the medicinal liquid, such as cancer patients since an error in supply of the medicinal liquid may cause an unexpected fatal death.

In order to solve such problems, as shown in FIG. 10, recently, the medicinal liquid supply apparatus further includes a channel control type medicinal liquid supply volume controller 500. The channel control type medicinal liquid supply volume controller 500 includes: a case 502 having a main body 502a and a cover 502b; a medicinal liquid control line 501 disposed inside the main body 502a of the case 502, the medicinal liquid control line 501 including an inflow part 501a and an outflow part 501b respectively having branch holes and a plurality of medicinal liquid branch hoses 501c, 501d, 501e and 501f of different flow amounts respectively connected to the inflow part 501a and the outflow part 501b; and a controller 503, on which numerical values are printed, rotatably mounted on the outer face of the cover 502b of the case 502 in such a way as to regulate opening and closing of the medicinal liquid branch hoses according to a rotation angle of the controller 503 to thereby control a supply volume of the medicinal liquid through the sum total of the flow amounts of the medicinal liquid branch hoses, whereby the medicinal liquid supply apparatus can discharge the medicinal liquid in a minutely fixed quantity. Accordingly, the paramedic can set and fix a necessary supply amount of the medicinal liquid according to the patient's conditions.

However, the medicinal liquid supply apparatus having the fixed-type medicinal liquid supply volume controller 500 has a problem in that it is impossible to arbitrarily and additionally supply the medicinal liquid when the patient complains of a pain during the paramedic's absence since the supply volume of the medicinal liquid is set by the paramedic.

SUMMARY OF THE INVENTION

Accordingly, the present invention has been made to solve the above-mentioned problems occurring in the prior arts, and it is an object of the present invention to provide a medicinal liquid supply apparatus, which includes a fixed-type medicinal liquid supply volume controller adapted to allow a paramedic to minutely control a supply volume of medicinal liquid in a fixed quantity according to a patient's disease conditions and an arbitrary medicinal liquid supply volume controller adapted to allow a patient or the third party to arbitrarily and additionally supply the medicinal liquid according to the patient's pain conditions, thereby more effectively supplying the medicinal liquid to the patient.

To accomplish the above object, according to the present invention, there is provided a medicinal liquid supply apparatus including: a fixed-type medicinal liquid supply volume controller mounted to a medicinal liquid hose connected to an outlet of a medicinal liquid supplier, the fixed-type medicinal liquid supply volume controller having a plurality of medicinal liquid branch hoses and a medicinal liquid transfer hose respectively connected to an inflow part and an outflow part of a medicinal liquid control line, the medicinal liquid branch hoses being opened and closed by a controller, the medicinal liquid transfer hose being always opened; a double medicinal liquid hose connected to an outlet of the fixed-type medicinal liquid supply volume controller, the double medicinal liquid hose having a branch tube connected to the medicinal liquid transfer hose; and an arbitrary medicinal liquid supply volume controller connected to the double medicinal liquid hose in such a way as to introduce the medicinal liquid transferred through the branch pipe of the double medicinal liquid hose into the medicinal liquid storing tube, whereby the patient or the third party can arbitrary and additionally supply the medicinal liquid using a button body.

As described above, the medicinal liquid supply apparatus according to the present invention can supply the medicinal liquid more effectively since the paramedic can minutely discharge the medicinal liquid in a fixed quantity according to the patient's disease conditions using the fixed-type medicinal liquid supply volume controller and anyone can additionally inject the medicinal liquid to the patient according to the patient's pain conditions using the arbitrary medicinal liquid supply volume controller as occasion demands.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Reference will be now made in detail to the preferred embodiment of the present invention with reference to the attached drawings.

Figure 1:
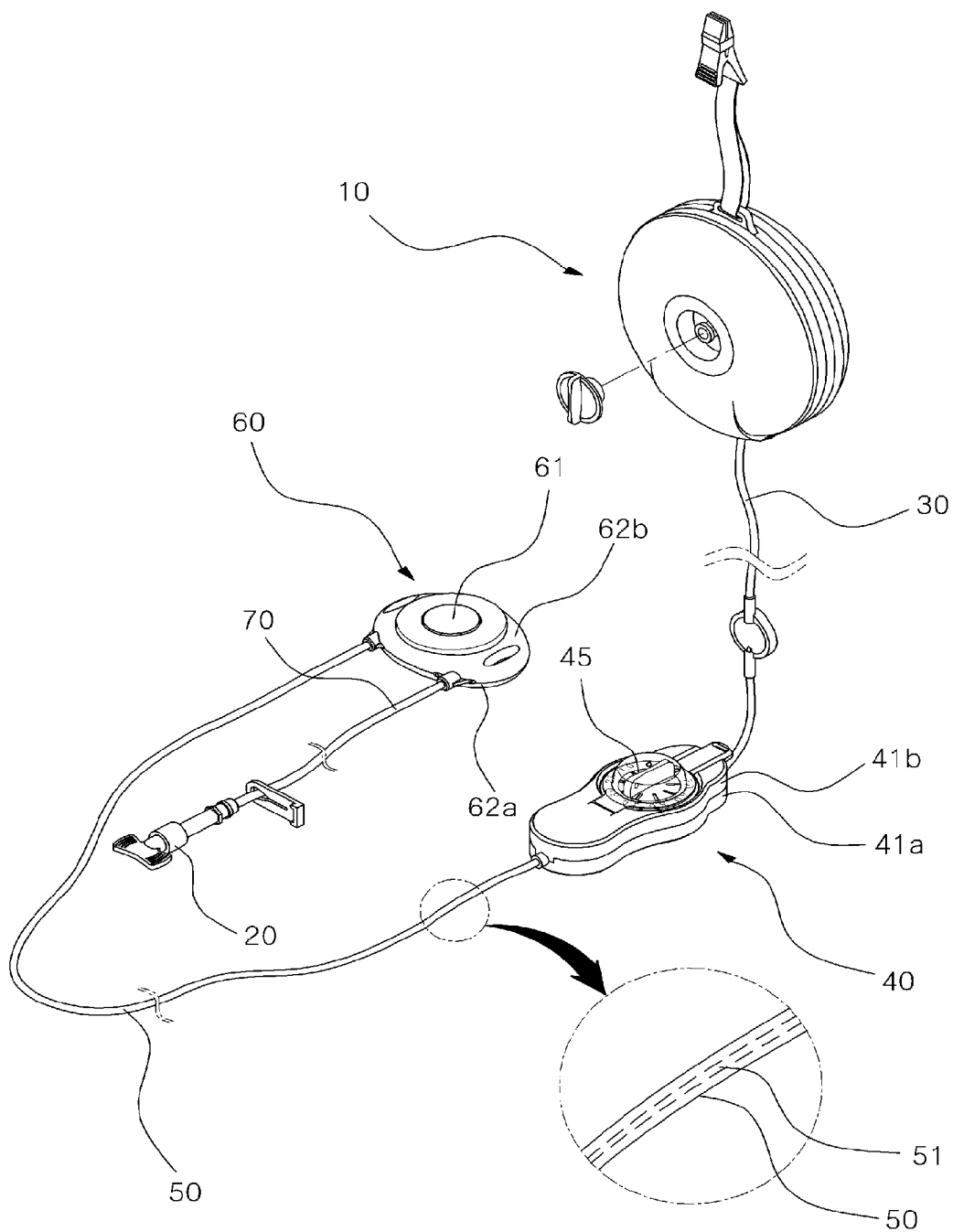
FIG. 1 is a perspective view of an outward appearance of a medicinal liquid supply apparatus according to a preferred embodiment of the present invention.

As shown in FIG. 1, a medicinal liquid supply apparatus according to the present invention includes a medicinal liquid supplier 10 filled with medicinal liquid of a predetermined volume; a syringe connector 20 for injecting the medicinal liquid to a patient; and a first medicinal liquid hose 30 connected between the medicinal liquid supplier 10 and the syringe connector 20.

Figure 2:
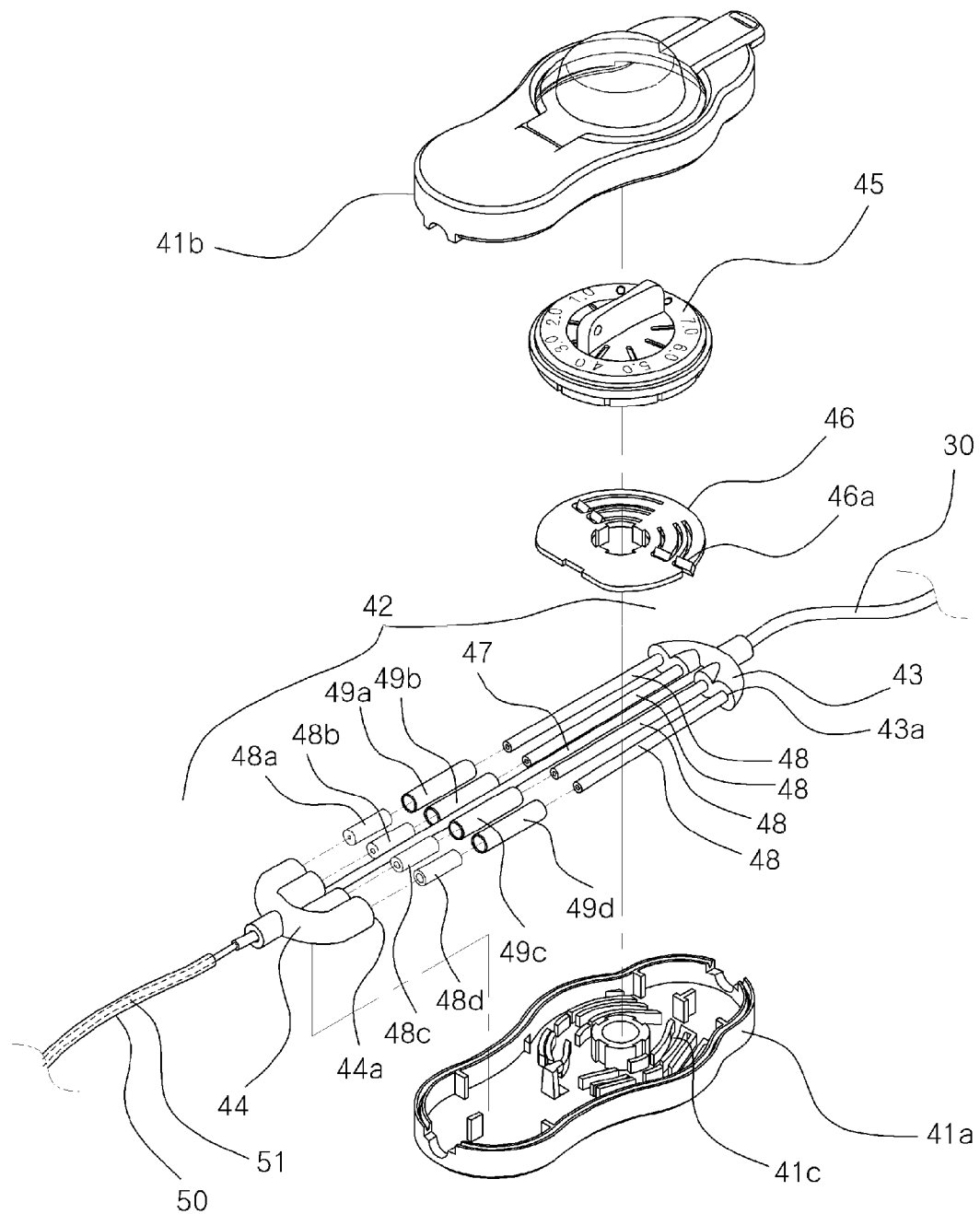
FIG. 2 is an exploded perspective view of a fixed-type medicinal liquid supply volume controller of the medicinal liquid supply apparatus according to the present invention.

As shown in FIG. 2, a fixed-type medicinal liquid supply volume controller 40 is connected to an outlet of the first medicinal liquid hose 30. The fixed-type medicinal liquid supply volume controller 40 includes: cases 41a and 41b correspondingly joined with each other; a medicinal liquid control line 42 received inside the cases 41a and 41b; an inflow part 43 and an outflow part 44 respectively formed on the opposite ends of the medicinal liquid control line 42 and respectively having a plurality of branch holes 43a and 44a; a controller 45 joined to the outer face of the case 41b; a pressure plate 46 pressed according to a rotation angle of the controller 45 and having a plurality of pressure pieces 46a; and a plurality of medicinal liquid branch hoses 48 and a medicinal liquid transfer hose 47 respectively connected to the branch holes 43a and 44a, the medicinal liquid branch hoses 48 being opened and closed by an action of the pressure plate 46, the medicinal liquid transfer hose 47 being always opened.

Figure 6:
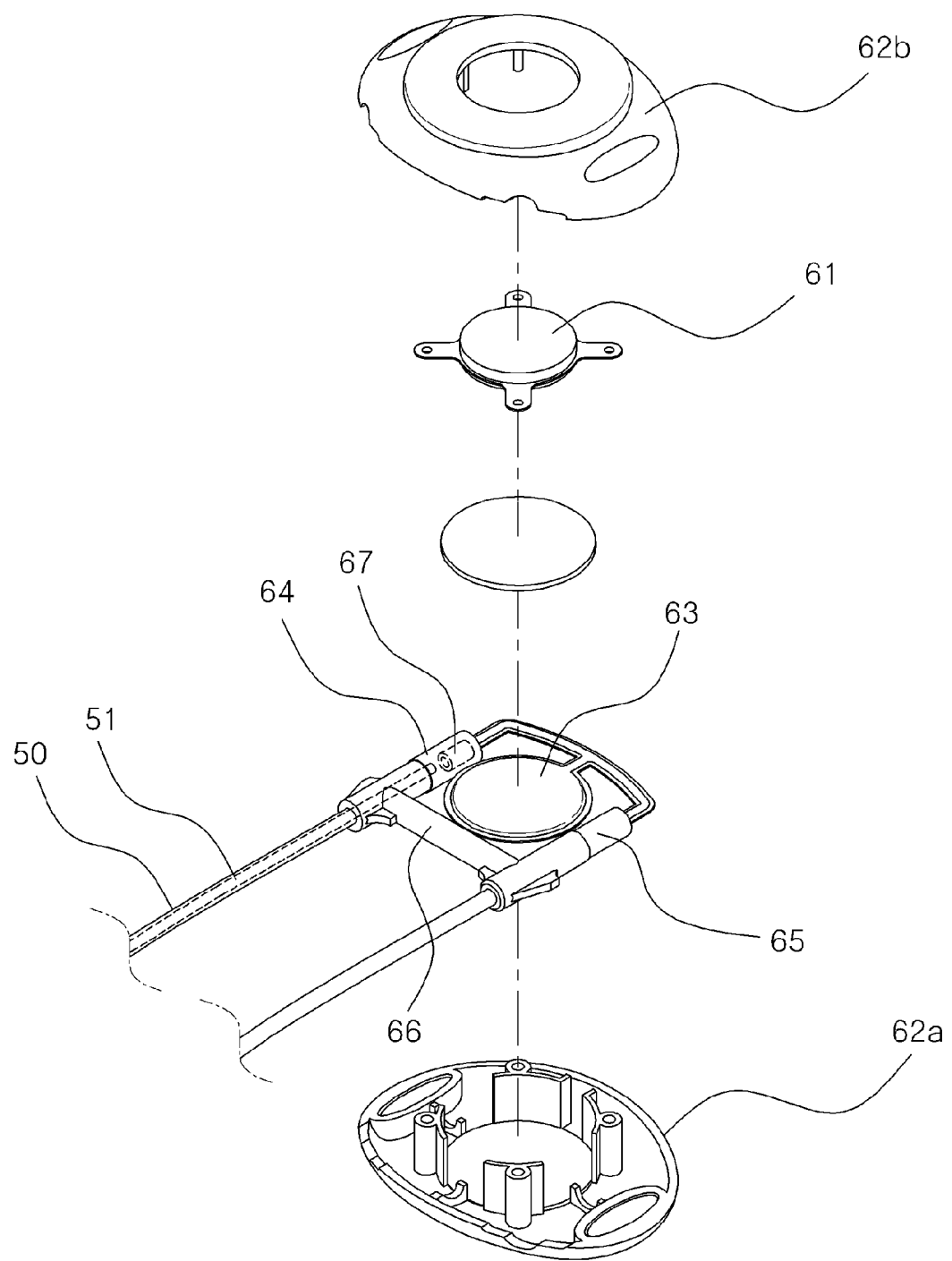
FIG. 6 is an exploded perspective view of an arbitrary medicinal liquid supply volume controller of the medicinal liquid supply apparatus according to the present invention.

One end of a double medicinal liquid hose 50 is connected to an outlet of the fixed-type medicinal liquid supply volume controller 40 and includes a branch tube 51 connected to the medicinal liquid transfer hose 47. As shown in FIG. 6, an arbitrary medicinal liquid supply volume controller 60 is connected to the other end of the double medicinal liquid hose 50. Accordingly, the medicinal liquid transferred through the branch tube 51 of the double medicinal liquid hose 50 is introduced into a medicinal liquid storing tube 63 received in cases 62a and 62b, which are correspondingly joined with each other, through a branch tube 64, and then, temporarily stored in the medicinal liquid storing tube 63 in a state where it is prevented in a back flow and in an inflow and an outflow by a check valve 65 formed on an outlet of the medicinal liquid storing tube 63. When the medicinal liquid storing tube 63 is pressurized by a button body 61 outwardly exposed from the cases 62a and 62b, the medicinal liquid can be additionally supplied through a second medicinal liquid hose 70 connected with the syringe connector 30. In the meantime, the medicinal liquid transferred through the double medicinal liquid hose 50 can be continuously supplied in such a way as to be transferred to the second medicinal liquid hose 70 through a bypass tube 66 connected to the double medicinal liquid hose 50.

Figure 3:
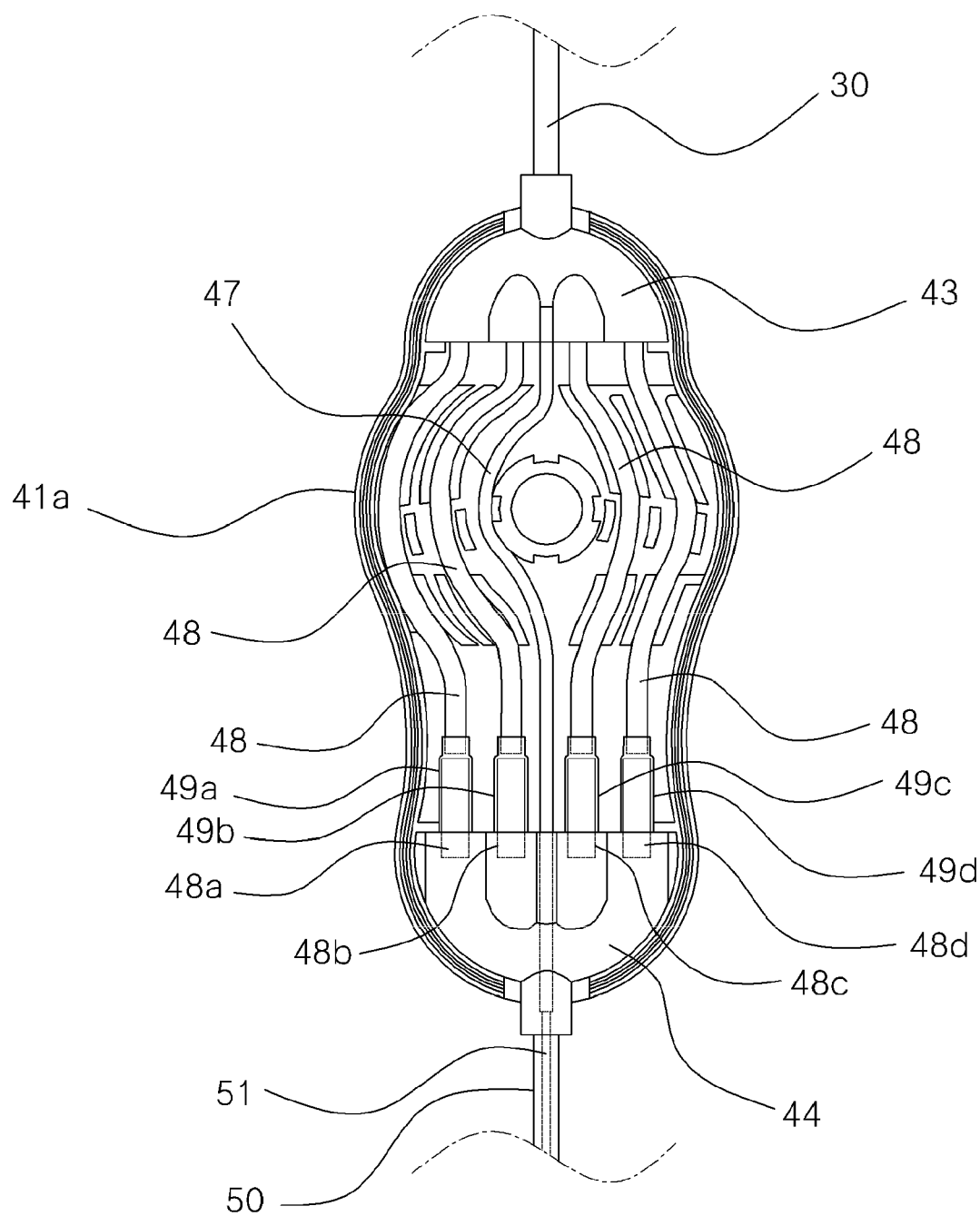
FIG. 3 is a view showing a state where a medicinal liquid control line is received in the fixed-type medicinal liquid supply volume controller.
Figure 4:
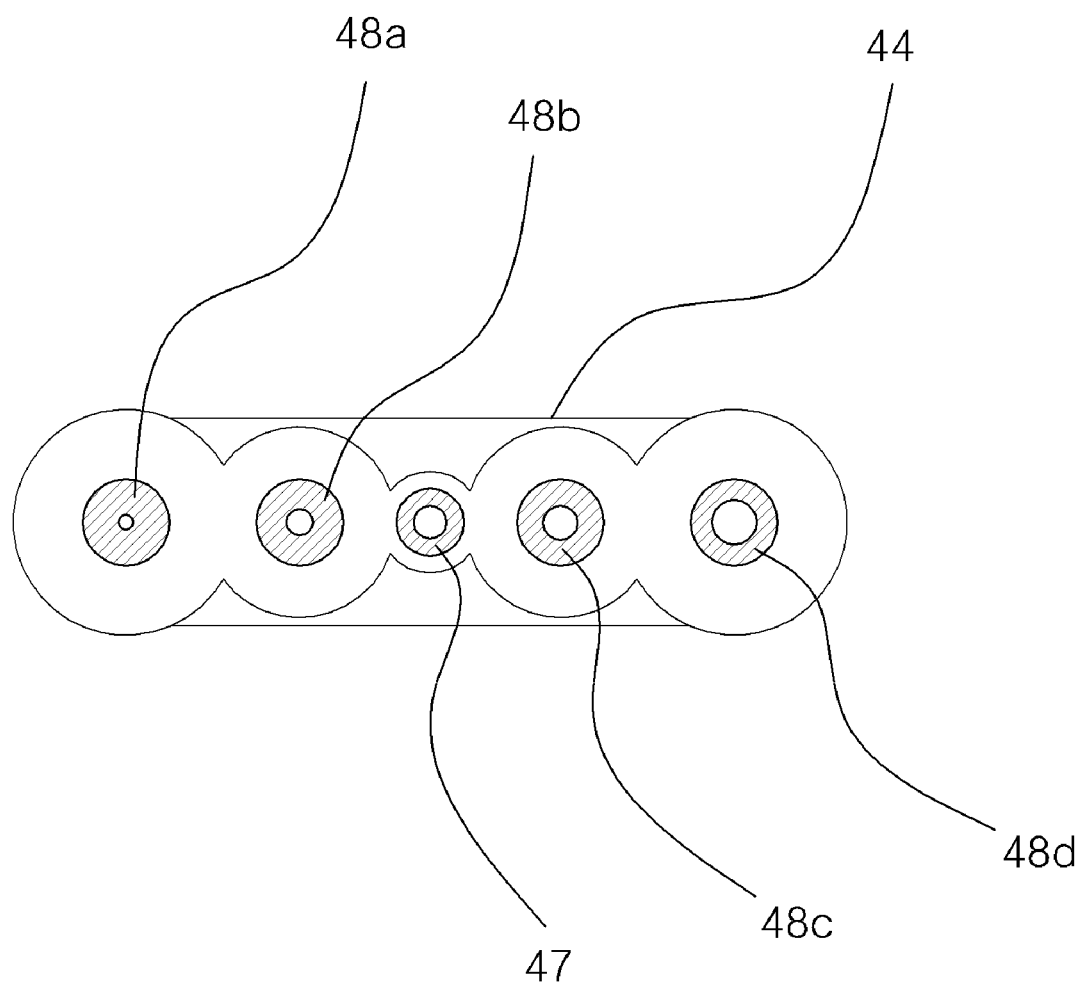
FIG. 4 is a sectional view showing a state where medicinal liquid control tubes of medicinal liquid branch hoses are received in the fixed-type medicinal liquid supply volume controller.

In this instance, as shown in FIGS. 3 and 4, all of the medicinal liquid branch hoses 48 of the medicinal liquid control line 42 formed in the fixed-type medicinal liquid supply volume controller 40 have the same channel section and length. Medicinal liquid control tubes 48a, 48b, 48c and 48d with different channel sections are respectively joined to ends of the medicinal liquid branch hoses 48 and aligned along guide lines 41c evenly formed on one inner face of the cases 41a and 41b in a row.

In this instance, the medicinal liquid control tubes 48a, 48b, 48c and 48d are glass tubes for reasons of sanitation.

Furthermore, since the medicinal liquid branch hoses 48 and the medicinal liquid control line are made of a soft material, the medicinal liquid control tubes 48a, 48b, 48c and 48d can be respectively forcedly fit to the ends of the medicinal liquid branch hoses 48 and the branch holes 43a of the inflow part 43 or the branch holes 44a of the outflow part 44 of the medicinal liquid control line 42. The other ends of the medicinal liquid branch hoses 48 and the branch holes 44a of the outflow part 44 or the branch holes 43a of the inflow part 43 of the medicinal liquid control line 42, to which the medicinal liquid control tubes 48a, 48b, 48c and 48d are not joined, may be made of the same material and molded integrally.

In this instance, in case where it is impossible to forcedly fit the medicinal liquid control tubes 48a, 48b, 48c and 48d and the medicinal liquid branch hoses 48 with each other in view of a manufacture, they can be forcedly joined with each other using elastic tubes 49a, 49b, 49c and 49d.

Moreover, a flow amount control tube 67 is mounted on the branch tube 64 of the arbitrary medicinal liquid supply volume controller 60 to pass only the medicinal liquid of a set flow amount, and hence, it can delay a time period to refill the medicinal liquid storing tube 63 with the medicinal liquid after the medicinal liquid stored in the medicinal liquid storing tube 63 is supplied, whereby it can prevent a medical accident caused by an excessive supply of the medicinal liquid.

In this instance, the flow amount control tube 67 is made of glass for the reasons of sanitation and easiness in manufacture, and can pass the medicinal liquid of 5 mml per hour.

Figure 5:
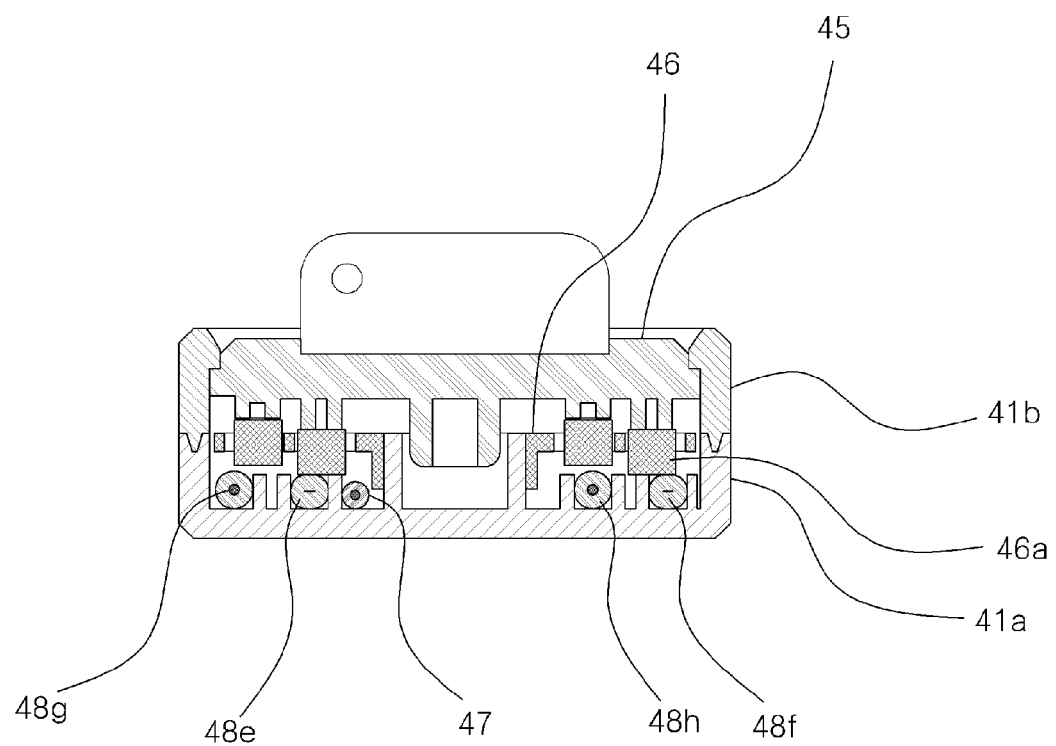
FIG. 5 is a sectional view showing an operational state of the fixed-type medicinal liquid supply volume controller.
Figure 5A:
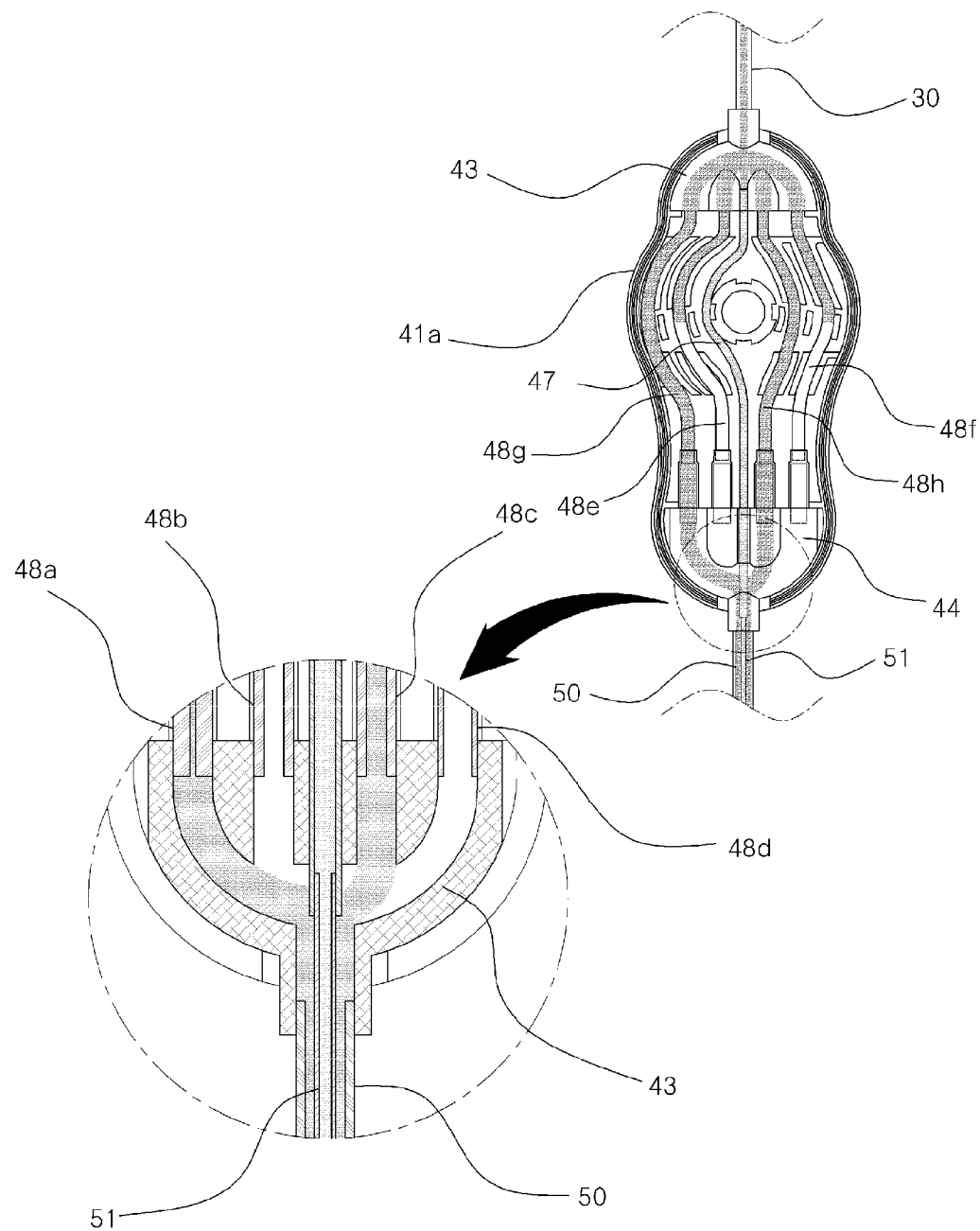
FIG. 5a is a view showing a flow of medicinal liquid when the fixed-type medicinal liquid supply volume controller of FIG. 5 is actuated.

Accordingly, as shown in FIGS. 5 and 5a, in the medicinal liquid supply apparatus according to the present invention, when the controller 45 of the fixed-type medicinal liquid supply volume controller 40 is rotated, the medicinal liquid branch hoses 48e and 48f, which are pressurized by the pressure pieces 46a of the pressure plate 46 according to the rotation angle of the controller 45, is closed, but the medicinal liquid branch hoses 48g and 48h, which are not pressurized by the pressure pieces 46a, are opened, and hence, the flow amounts of the medicinal liquid flowing through the opened medicinal liquid branch hoses 48g and 48h are added together. The added medicinal liquid passes through the double medicinal liquid hose 50 and the second branch tube 66 and the second medicinal liquid hose 70 of the arbitrary medicinal liquid supply volume controller 60 in order, and then, is continuously discharged through the syringe connector 20 in the fixed quantity.

Figure 7:
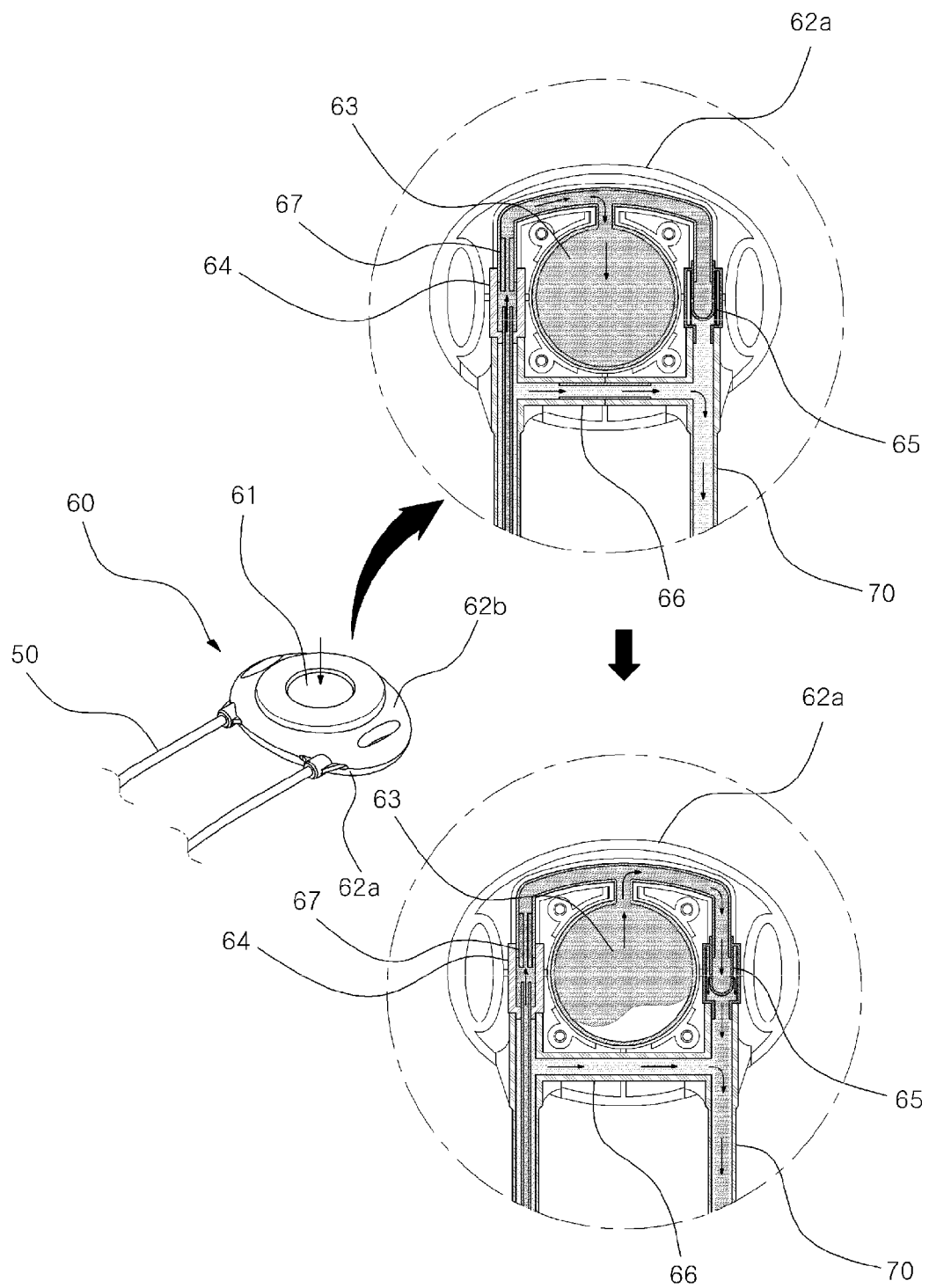
FIG. 7 is a view showing a flow of medicinal liquid of the arbitrary medicinal liquid supply volume controller.
Figure 8:
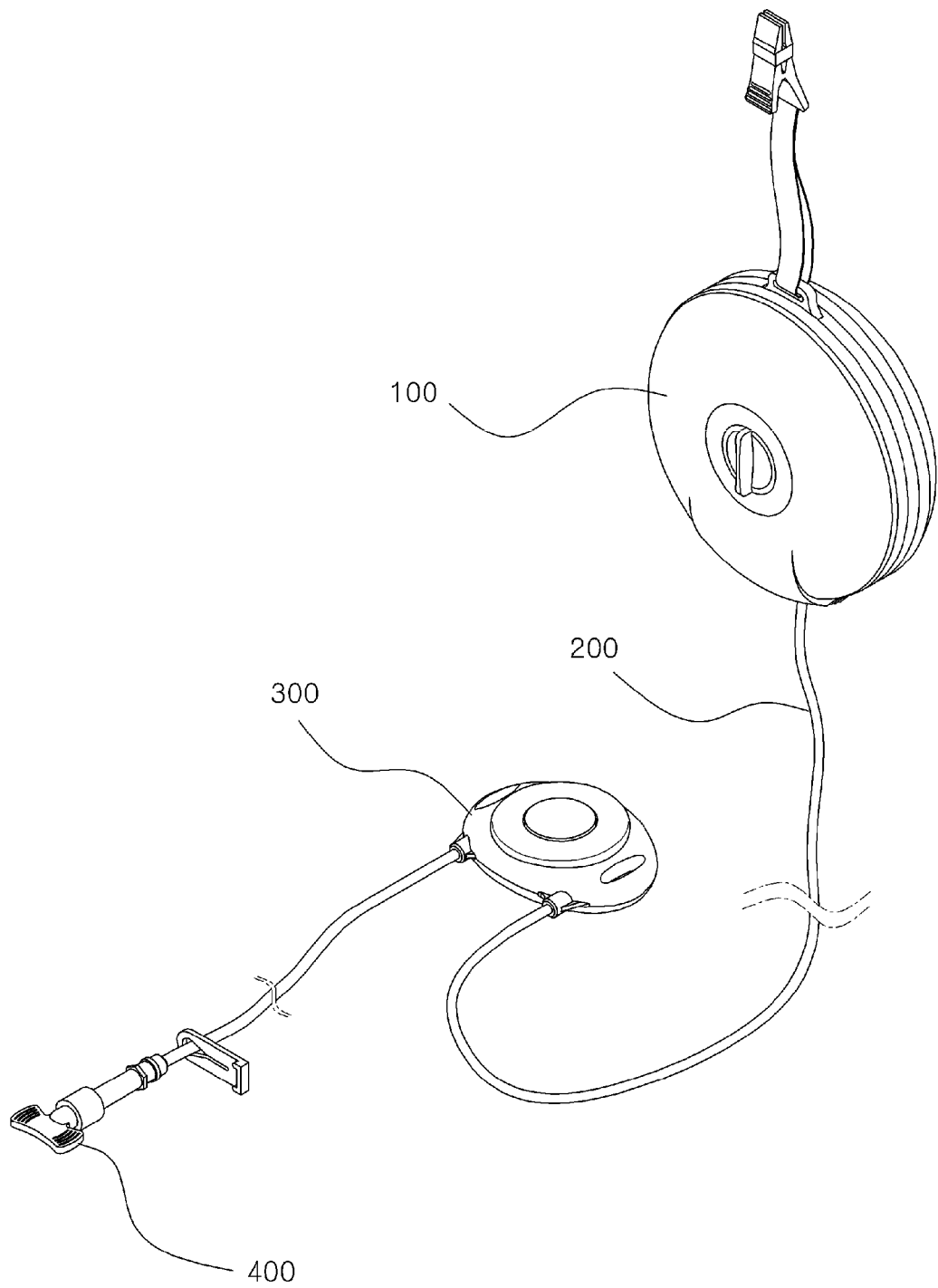
FIG. 8 is a configurative view of a conventional medicinal liquid supply apparatus.
Figure 9:
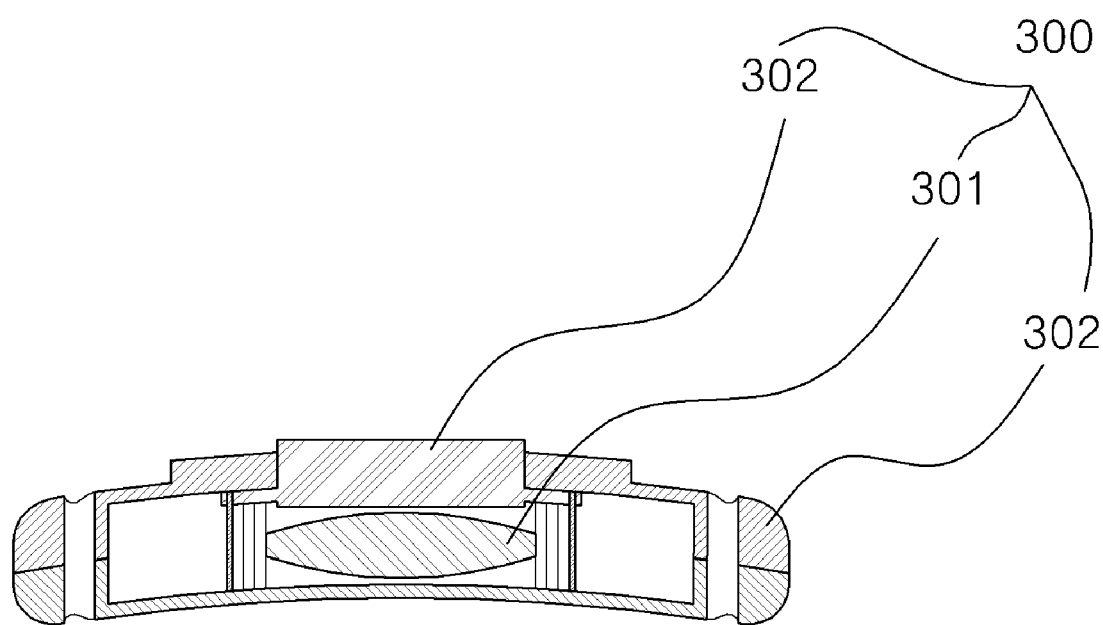
FIG. 9 is a configurative view of a conventional button-type medicinal liquid supply volume controller.
Figure 10:
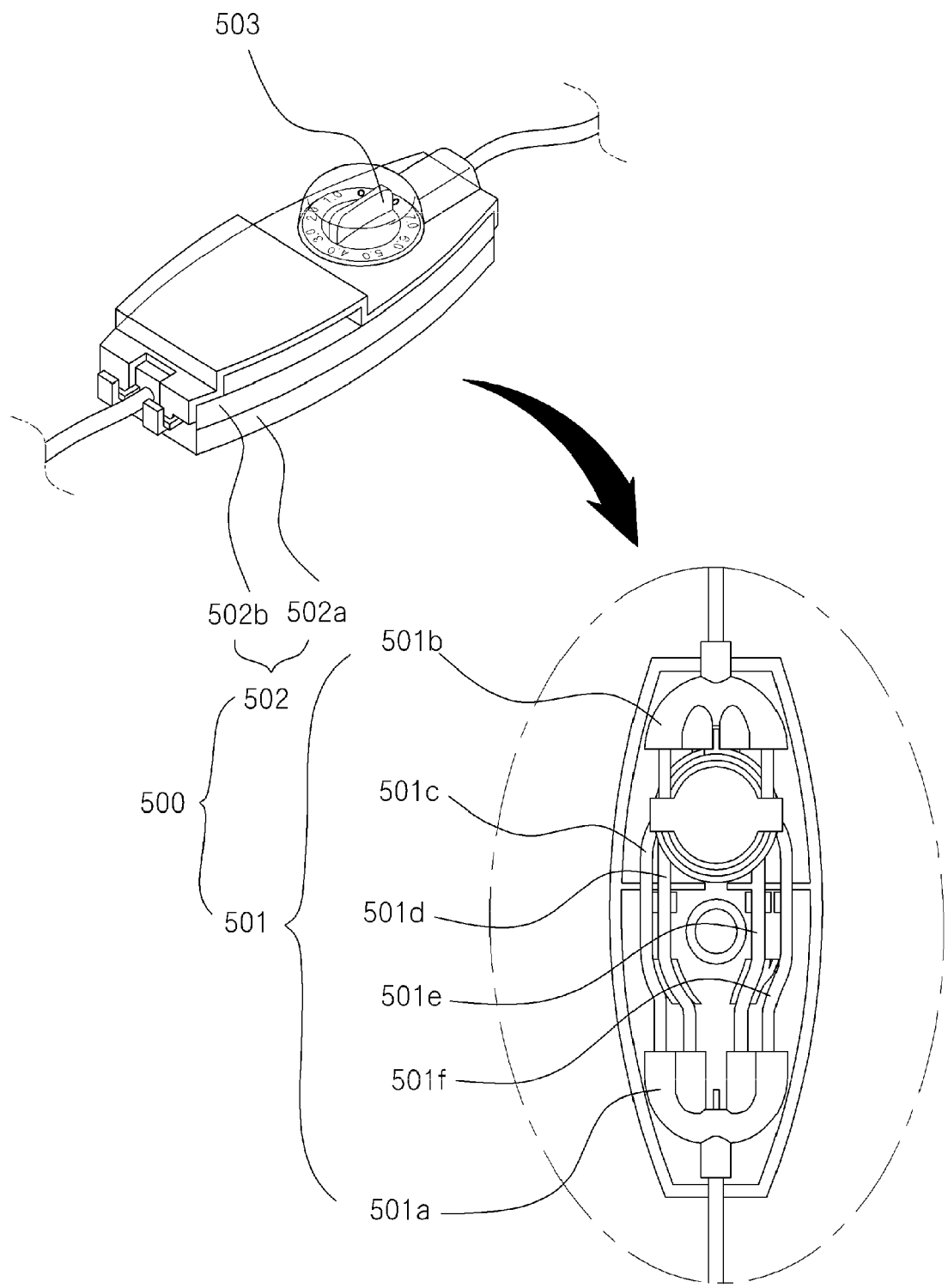
FIG. 10 is a configurative view of a conventional channel control type medicinal liquid supply volume controller.

In the meantime, the medicinal liquid is continuously transferred through the branch tube 51 of the double medicinal liquid hose 50 without regard to the controller 45 after passing through the medicinal liquid transfer hose 47 formed on the medicinal liquid control line 42 of the fixed-type medicinal liquid supply volume controller 40. After that, as shown in FIG. 7, the medicinal liquid is temporarily stored in the medicinal liquid storing tube 63 after being introduced into the medicinal liquid storing tube 63 through the branch tube 64 of the arbitrary medicinal liquid supply volume controller 60. As occasion demands, when the button body 61 is pressed, the medicinal liquid storing tube 63 is pressurized by the button body 61, and hence, the medicinal liquid stored in the medicinal liquid storing tube 63 is added to the medicinal liquid, which is being discharged in the fixed quantity by the fixed-type medicinal liquid supply volume controller 40, through the second medicinal liquid hose 70 and discharged temporarily.

Moreover, in case of the fixed-type medicinal liquid supply volume controller 40, since a variable in a difference of flow amount supplied through the medicinal liquid branch hoses 48 of the medicinal liquid control line 42 is not lengths of the medicinal liquid branch hoses 48 but channel sections of the medicinal liquid control tubes 48a, 48b, 48c and 48d connected and joined to the ends of the medicinal liquid branch hoses 48, the medicinal liquid branch hoses with different flow amounts may have the same length.

Accordingly, all of the medicinal liquid branch hoses 48 can be received in the case evenly in a row and guarantee a smooth flow of the medicinal liquid transferred through the medicinal liquid branch hoses 48 to thereby control the volume of the medicinal liquid in the fixed quantity. The medicinal liquid branch hoses 48 aligned as described above can prevent the inside accumulation of the medicinal liquid since there are no twisted portions or rolled portions and minutely control the volume of the medicinal liquid in the fixed quantity since the channel sections of the medicinal liquid branch hoses 48 can be reduced minutely.

While the present invention has been described with reference to the particular illustrative embodiment, it is not to be restricted by the embodiment but only by the appended claims. It is to be appreciated that those skilled in the art can change or modify the embodiment without departing from the scope and spirit of the present invention.

What is claimed is:

1. A medicinal liquid supply apparatus comprising:
a fixed-type medicinal liquid supply volume controller (40) connected to one end of a first medicinal liquid hose (30) whose the other end is connected to an outlet of a medicinal liquid supplier (10), the fixed-type medicinal liquid supply volume controller (40) comprising: cases (41a; 41b); a medicinal liquid control line (42) received inside the cases (41a; 41b); an inflow part (43) and an outflow part (44) respectively formed on opposite ends of the medicinal liquid control line (42) and each respectively comprising a plurality of branch holes (43a; 44a); a controller 45 joined to an outer face of the case (41a or 41b); a pressure plate (46) pressed according to a rotation angle of the controller (45) and comprising a plurality of pressure pieces (46a); and a plurality of medicinal liquid branch hoses (48) and a medicinal liquid transfer hose (47) one end of each respectively connected to the branch holes (43a) of the inflow part and another end of each respectively connected to the branch holes (44a) of the outflow part, the medicinal liquid branch hoses (48) between the inflow part and the outflow part being opened and closed by an action of the pressure plate (46), the medicinal liquid transfer hose (47) between the inflow part and the outflow part being always opened;

a double medicinal liquid hose (50) comprising a plurality of tubes, wherein the plurality of tubes are of different radii and share substantially a same longitudinal axis, one end of a first tube of the plurality of tubes being connected to an outlet of the fixed-type medicinal liquid supply volume controller (40), one end of a second tube of the plurality of tubes of the double medicinal liquid hose (50) comprising a branch tube (51) connected to the medicinal liquid transfer hose (47); and an arbitrary medicinal liquid supply volume controller (60) connected to an other end of the double medicinal liquid hose (50), the arbitrary medicinal liquid supply volume controller (60) comprising: a medicinal liquid storing tube (63) for storing the medicinal liquid, which is transferred through the branch tube (51) of the double medicinal liquid hose (50), via a branch tube (64) of the arbitrary medicinal liquid supply volume controller (60); a check valve (65) adapted to allow the medicinal liquid storing tube (63) to temporarily store the medicinal liquid therein and prevent a back flow of the medicinal liquid; a button body (61) adapted to pressurize the medicinal liquid storing tube (63) to thereby arbitrarily and additionally supply the medicinal liquid through a second medicinal liquid hose (70); and a bypass tube (66) connected to the double medicinal liquid hose (50) for transferring the medicinal liquid transferred through the double medicinal liquid hose (50) to the second medicinal liquid hose (70) to thereby continuously supply the medicinal liquid.

2. The medicinal liquid supply apparatus according to claim 1, wherein all of the medicinal liquid branch hoses (48) formed in the fixed-type medicinal liquid supply volume controller (40) have the same channel section and length and respectively have medicinal liquid control tubes (48a; 48b; 48c; 48d) of different channel sections respectively joined to one end of each of the medicinal liquid branch hoses (48) in such a way as to be respectively aligned along guide lines (41c) formed on the inner face of the cases (41a; 41b).

3. The medicinal liquid supply apparatus according to claim 2, wherein the medicinal liquid control tubes (48a; 48b; 48c; 48d) joined to the medicinal liquid branch hoses (48) are glass tubes.

4. The medicinal liquid supply apparatus according to claim 2, wherein the medicinal liquid control tubes (48a; 48b; 48c; 48d) and the medicinal liquid branch hoses (48) are forcedly fit to each other using elastic tubes (49a; 49b; 49c; 49d).

5. The medicinal liquid supply apparatus according to claim 3, wherein the medicinal liquid control tubes (48a; 48b; 48c; 48d) and the medicinal liquid branch hoses (48) are forcedly fit to each other using elastic tubes (49a; 49b; 49c; 49d).

6. The medicinal liquid supply apparatus according to claim 1, wherein a flow amount control tube (67) is mounted on the branch tube (64) of the arbitrary medicinal liquid supply volume controller (60) to pass only the medicinal liquid of a fixed flow amount.

7. The medicinal liquid supply apparatus according to claim 6, wherein the flow amount control tube (67) is a glass tube, which can pass the medicinal liquid of 5 mml per hour.

8. A medicinal liquid supply apparatus, which comprises a fixed-type medicinal liquid supply volume controller (40) connected to one end of a first medicinal liquid hose (30) whose the other end is connected to an outlet of a medicinal liquid supplier (10), the fixed-type medicinal liquid supply volume controller (40) including: cases (41*a*; 41*b*); a medicinal liquid control line (42) received inside the cases (41*a*; 41*b*); an inflow part (43) and an outflow part (44) respectively formed on opposite ends of the medicinal liquid control line (42) and each respectively comprising a plurality of branch holes (43*a*; 44*a*); a controller 45 joined to an outer face of the case (41*a* or 41*b*); a pressure plate (46) pressed according to a rotation angle of the controller (45) and comprising a plurality of pressure pieces (46*a*); and a plurality of medicinal liquid branch hoses (48) and a medicinal liquid transfer hose (47) one end of each respectively connected to the branch holes of the inflow part (43*a*) and another end of each respectively connected to the branch holes of the outflow part (44*a*), the medicinal liquid branch hoses (48) between the inflow part and the outflow part being opened and closed by an action of the pressure plate (46), the medicinal liquid transfer hose (47) between the inflow part and the outflow part being always opened, the outflow part further comprising a double medicinal liquid hose (50) comprising a plurality of tubes, wherein the plurality of tubes are of different radii and share substantially a same longitudinal axis, one end of a first tube of the plurality of tubes being connected to an outlet of the fixed-type medicinal liquid supply volume controller (40), one end of a second tube of the plurality of tubes of the double medicinal liquid hose (50) comprising a branch tube (51) connected to the medicinal liquid transfer hose (47), wherein all of the medicinal liquid branch hoses (48) formed in the fixed-type medicinal liquid supply volume controller (40) have the same channel section and length and respectively have medicinal liquid control tubes (48*a*; 48*b*; 48*c*; 48*d*) of different channel sections respectively joined to one end of each of the medicinal liquid branch hoses (48) in such a way as to be respectively aligned along guide lines (41*c*) formed on the inner face of the cases (41*a*; 41*b*).

9. The medicinal liquid supply apparatus according to claim 8, wherein the medicinal liquid control tubes (48*a*; 48*b*; 48*c*; 48*d*) joined to the medicinal liquid branch hoses (48) are glass tubes.

10. The medicinal liquid supply apparatus according to claim 8, wherein the medicinal liquid control tubes (48*a*; 48*b*; 48*c*; 48*d*) and the medicinal liquid branch hoses (48) are forcedly fit to each other using elastic tubes (49*a*; 49*b*; 49*c*; 49*d*).

11. The medicinal liquid supply apparatus according to claim 9, wherein the medicinal liquid control tubes (48*a*; 48*b*; 48*c*; 48*d*) and the medicinal liquid branch hoses (48) are forcedly fit to each other using elastic tubes (49*a*; 49*b*; 49*c*; 49*d*).

\* \* \* \* \*